(12) United States Patent
Barkats et al.

(10) Patent No.: US 7,241,591 B2
(45) Date of Patent: Jul. 10, 2007

(54) ADENOVIRUS COMPRISING A GENE CODING FOR GLUTATHIONE PEROXIDASE

(75) Inventors: Martine Barkats, Paris (FR); Jacques Mallet, Paris (FR); Frédéric Revah, Antony (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 10/768,635

(22) Filed: Feb. 2, 2004

(65) Prior Publication Data

US 2004/0175363 A1    Sep. 9, 2004

Related U.S. Application Data

(63) Continuation of application No. 08/776,786, filed as application No. PCT/FR95/01002 on Jul. 26, 1995, now abandoned.

(30) Foreign Application Priority Data

Aug. 12, 1994  (FR) .................................. 94 09982

(51) Int. Cl.
C12N 15/861 (2006.01)
C12N 15/52 (2006.01)
C12N 5/08 (2006.01)
C12N 5/10 (2006.01)

(52) U.S. Cl. .................. 435/69.1; 435/320.1; 435/368; 435/456; 424/93.2

(58) Field of Classification Search ..................... None
See application file for complete search history.

(56) References Cited

U.S. PATENT DOCUMENTS 5,187,078 A    2/1993  Ohya et al. ................ 435/69.1
5,543,328 A *  8/1996  McClelland et al. ..... 435/320.1
6,290,949 B1   9/2001  French et al. .............. 424/93.2
2003/0083303 A1* 5/2003 Zhang et al. ................. 514/44

FOREIGN PATENT DOCUMENTS

| WO | WO88/07541 | 10/1988 |
| WO | WO90/06757 | 6/1990 |
| WO | WO93/20195 | 10/1993 |

OTHER PUBLICATIONS

Mullenbach et al., "cDNAs of three glutathione peroxidases: selenocysteine incorporation," UCLA Symp. Mol. Cell. Biol., New Ser. 82: 313-326, 1988.*
Erzurum et al.; Protection of Human Endothelial Cells from Oxidant Injury by Adenovirus-Mediated Transfer of the Human Catalase cDNA; Nucleic Acids Research, 21, 7, 1607-1612 (1993).
Aguzzi et al.; Transgenic and Knock-out Mice: Models of Neurological Disease; Brain Pathology 4, 3-20 (1994).
Bell et al.; cDNA Sequence Coding for Human Kidney Catalase; Chemical Abstracts, 105, 19, (1986).
Danos et al., Réimplantation de cellules génétiquement modifiées dans des néo-organes vascularisés; Medicine/Science 9, 208-210 (1993).

* cited by examiner

*Primary Examiner*—Scott D. Priebe
(74) *Attorney, Agent, or Firm*—Finnegan, Henderson, Farabow, Garrett & Dunner, L.L.P.

(57) ABSTRACT

The present invention relates to a defective adenovirus comprising at least a DNA sequence coding for all or an active part of glutathione peroxidase or a derivative thereof. It also relates to their utilization in therapy and to the corresponding pharmaceutical compositions.

4 Claims, 1 Drawing Sheet

ADENOVIRUS COMPRISING A GENE CODING FOR GLUTATHIONE PEROXIDASE

Figure 1:
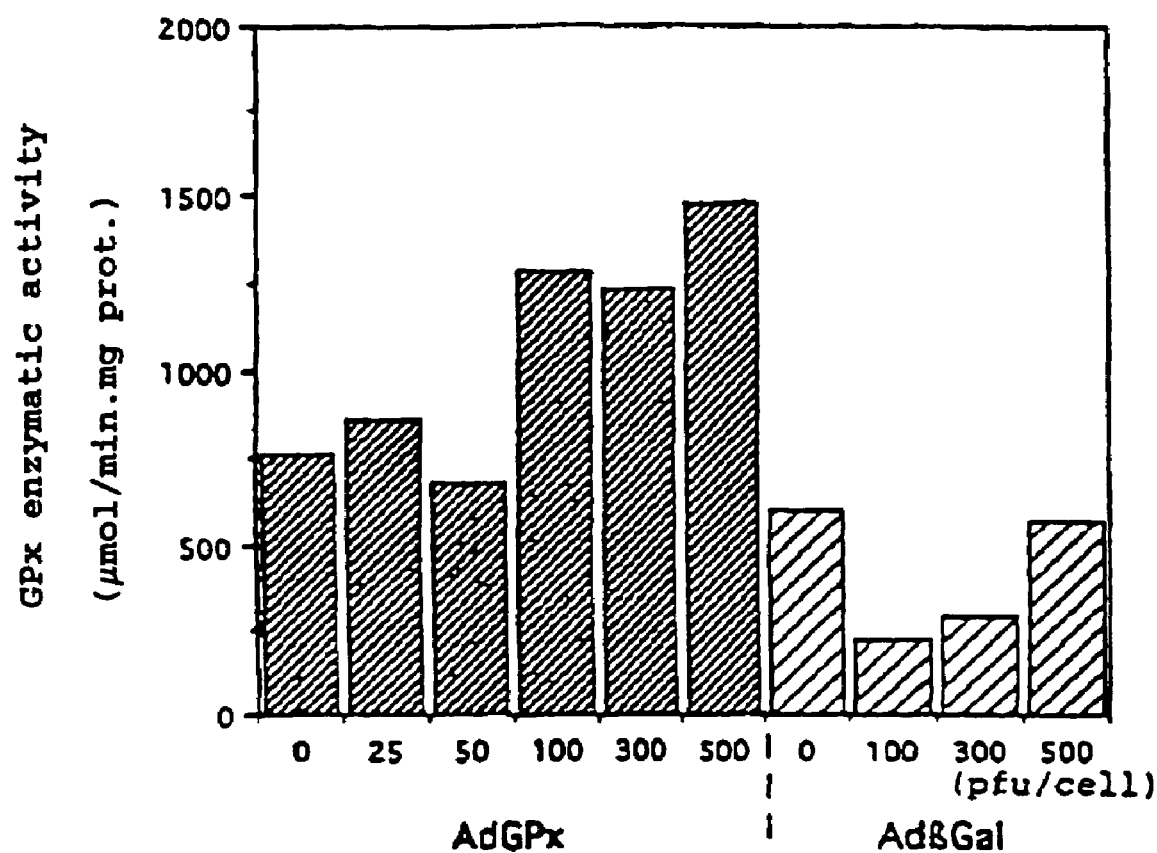

This is a continuation of application Ser. No. 08/776,786, now abandoned which is the U.S. National Stage Application of International Application PCT/FR95/01002, filed Jul. 26, 1995, and claiming priority to French Application FR94/09982, filed Aug. 12, 1994, and are all incorporated herein by reference.

The present invention relates to recombinant adenoviruses comprising a DNA sequence encoding glutathione peroxidase and its uses in gene therapy.

Glutathione peroxidase is one of the enzymes which are actively involved in the regulation of the concentration of oxygen-derived free radicals formed during various physiological or pathological processes.

Normally, the formation of these radicals, which are highly reactive, such as the superoxide anion, hydrogen peroxide and the hydroxyl radical is controlled as follows: superoxide anion is rapidly converted to hydrogen peroxide, by means of superoxide dismutase, then this hydrogen peroxide is converted to oxygen and water, by catalase or in particular glutathione peroxidase.

Usually, these enzymes are present in practically all tissues.

However, under certain conditions, these regulatory mechanisms are not totally efficient. In particular, there may be a disequilibrium between their respective concentrations, for example an excessive superoxide dismutase concentration compared with the available quantity of glutathione peroxidase, leading to a pathological production of hydrogen peroxide and of free radicals (hydroxyl radicals in particular).

These free radicals may directly induce a peroxidation of membrane lipids, inactivate enzymes by peroxidizing their sulphydryl groups, depolymerize polysaccharides and/or damage nucleic acids, causing in all cases serious pathologies. They may thus be responsible for inflammations, emphysemas, neoplasms and/or retinopathies. They also appear to be involved in atherosclerosis, cerebral ischaemia, cranial traumas, respiratory distress syndrome, cardiovascular diseases, diabetes, cirrhosis of the liver and formation of cataracts as well as in the aging process. Free radicals are also thought to be linked to the apoptosis process and could be involved in the cell death accompanying the acquired immunodeficiency syndrome (AIDS), [The J. of Biol. Chem., 269, 2(14), 798–801, (1994)]. More recently, it has been demonstrated that reactions between these radicals or with neurotransmitters led to the formation of endogenous neurotoxins. Free radicals are therefore also involved in neurological pathologies such as Alzheimer's disease, Parkinson's disease, amyotrophic lateral sclerosis (ALS) and/or trisomy 21.

Consequently, it would be particularly valuable to have available nowadays medicinal products which can increase or regulate the glutathione peroxidase concentration in the body and which are therefore effective for treating all the abovementioned pathologies.

The present invention is precisely consists in the development of vectors which are particularly efficient for delivering in vivo and in a localized manner, therapeutically active quantities of the specific gene encoding glutathione peroxidase or one of its derivatives.

In the corresponding application no. PCT/EP93/02519, it has been shown that adenoviruses could be used as vector for the transfer of a foreign gene in vivo into the nervous system and the expression of the corresponding protein.

The present invention relates more particularly to new constructs which are particularly suitable and efficient for controlling the expression of glutathione peroxidase.

More precisely, it relates to a recombinant adenovirus comprising a DNA sequence for controlling the expression of a glutathione peroxidase, its use for therapeutic treatments and/or the prevention of various pathologies.

The Applicant has thus demonstrated that it is possible to construct recombinant adenoviruses containing a sequence encoding a glutathione peroxidase, to administer these recombinant adenoviruses in vivo, and that this administration allows a stable and localized expression of therapeutically active quantities of glutathione peroxidase in vivo.

A first subject of the invention therefore consists in a defective recombinant adenovirus comprising at least one DNA sequence encoding all or an active part of a glutathione peroxidase or one of its derivatives.

For the purposes of the present invention, glutathione peroxidase designates any enzyme having glutathione peroxidase activity. By way of illustration of these enzymes, there may in particular be mentioned in man the glutathione peroxidases GPX1, GPX2, GPX3 and GPX4. GPX1 and GPX4 are expressed in most tissues with a clear predominance in the erythrocytes, the liver and the kidneys for GPX1 (Chambers et al; EMBO J 5: 1221–1227 (1986)) and in the testicles for GPX4 [Roveri et al; J. Biol. Chem. 267:6142–6146 (1992)]. GPX3 is produced in the kidneys, the lungs, the heart, the breast, the placenta as well as in the liver (Chu et al. Blood 79: 3233__3238 (1992)) as for GPX2, it has mainly been demonstrated in the gastrointestinal tissues and in the liver [Chu et al. J. Biol. Chem. 268: 2571–257 (1993)].

The glutathione peroxidase produced within the framework of the present invention may be a human or animal glutathione peroxidase. It may in particular be bovine glutathione peroxidase.

The DNA sequence encoding glutathione peroxidase, which is used within the framework of the present invention may be a cDNA, a genomic DNA (gDNA), or a hybrid construct consisting for example of a cDNA into which one or more introns would be inserted. The nucleic sequence of the cDNA encoding human glutathione peroxidase has been described by [Mullenbach et al., Oxy-Radicals in Molecular Biology and Pathology, 313–326, (1988)]. It may also be synthetic or semisynthetic sequences.

In a particularly advantageous manner, a cDNA or a gDNA is used.

According to a preferred embodiment of the invention, it is a genomic DNA (gDNA) sequence encoding a glutathione peroxidase. Its use may allow an enhanced expression in human cells.

Of course, prior to its incorporation into an adenovirus vector according to the invention, the DNA sequence may be advantageously modified, for example by site-directed mutagenesis, in particular for the insertion of appropriate restriction sites. The sequences described in the prior art are indeed not constructed for a use according to the invention, and prior adaptations may prove necessary in order to obtain high expression levels.

For the purposes of the present invention, derivative is understood to mean any sequence obtained by modification and encoding a product which preserves at least one of the biological properties of glutathione peroxidase. Modification should be understood to mean any mutation, substitution, deletion, addition or modification of a genetic and/or chemical nature. These modifications can be performed by techniques known to persons skilled in the art (see general molecular biology techniques below). The derivatives according to the invention can also be obtained by hybridization from nucleic acid libraries, using as probe the glutathione peroxidase native sequence or a fragment thereof.

These derivatives are especially molecules having a higher affinity for their binding sites, sequences allowing an enhanced expression in vivo, molecules having a greater resistance to proteases, molecules having a higher therapeutic efficacy or fewer side effects, or possibly new biological properties.

Among the preferred derivatives, there may be mentioned more particularly natural variants, molecules in which one or more residues have been substituted, derivatives obtained by deletion of regions having little or no involvement in the interaction with the binding sites considered or expressing an undesirable activity, and derivatives containing additional residues compared with the native sequence, such as for example a secretory signal and/or a joining peptide.

The DNA sequence, encoding all or part of a glutathione peroxidase or one of its derivatives, may also be an antisense sequence whose expression in the target cell makes it possible to control the expression of this enzyme. Preferably, the heterologous DNA sequence contains a gene encoding an antisense RNA capable of controlling the translation of the corresponding mRNA. The antisense sequence may be all or only part of the DNA sequence encoding a glutathione peroxidase, inserted in the reverse orientation in the vector according to the invention.

According to one embodiment of the invention, the DNA sequence encoding a glutathione peroxidase or one of its derivatives can also integrate a secretory signal which makes it possible to direct the synthesized glutathione peroxidase in the secretory pathways of the infected cells. In this manner, the synthesized glutathione peroxidase is advantageously released into the extracellular compartments.

Advantageously, the glutathione peroxidase encoding sequence is placed under the control of signals allowing its expression in the target cells. Preferably, these are heterologous expression signals, that is to say signals which are different from those naturally responsible for the expression of glutathione peroxidase. They may be in particular sequences responsible for the expression of other proteins, or of synthetic sequences. In particular, they may be promoter sequences of eukaryotic or viral genes. For example, they may be promoter sequences derived from the genome of the cell which it is desired to infect. Likewise, they may be promoter sequences derived from the genome of a virus, including the adenovirus used. In that respect, there may be mentioned for example the E1A, MLP, CMV, RSV-LTR promoters and the like. In addition, these expression sequences can be modified by addition of activation or regulatory sequences or of sequences allowing a tissue-specific expression. It may be particularly advantageous to use expression signals which are specifically or predominantly active in the target cells, so that the DNA sequence is expressed or produces its effect only when the virus has indeed infected a target cell.

In a first specific embodiment, the invention relates to a defective recombinant adenovirus comprising a cDNA or DNA8 sequence encoding a bovine glutathione peroxidase under the control of the RSV-LTR promoter.

In another specific embodiment, the invention relates to a defective recombinant adenovirus comprising a gDNA sequence encoding human glutathione peroxidase under the control of the RSV-LTR promoter.

A particularly preferred embodiment of the present invention consists in a defective recombinant adenovirus comprising the ITR sequences, a sequence allowing encapsidation, a DNA sequence encoding human glutathione peroxidase or a derivative thereof under the control of a promoter allowing predominant expression in the target tissues and in which the E1 gene and at least one of the E2, E4, L1–L5 genes is not functional.

The defective adenoviruses according to the invention are adenoviruses which are incapable of autonomously replicating in the target cell. Generally, the genome of the defective adenoviruses used within the framework of the present invention therefore lacks at least the sequences necessary for the replication of the said virus in the infected cell. These regions can be either removed (completely or partially), or rendered nonfunctional, or substituted with other sequences and especially with the glutathione peroxidase encoding DNA sequence.

Preferably, the defective virus of the invention conserves the sequences of its genome which are necessary for the encapsidation of the viral particles. Still more preferably, as indicated above, the genome of the defective recombinant virus according to the invention comprises ITR sequences, a sequence allowing encapsidation, the nonfunctional E1 gene and at least one of the nonfunctional E2, E4, L1–L5 genes.

There are various serotypes of adenoviruses, whose structure and properties vary somewhat. Among these serotypes, the use of type 2 or 5 human adenoviruses (Ad 2 or Ad 5) or of adenoviruses of animal origin (see Application FR 93 05954) is preferred within the framework of the present invention. Among the adenoviruses of animal origin which can be us d within the framework of the present invention, there may be mentioned adenoviruses of canine, bovine, murin [example: MAV1, Beard et al., Virology 75 (1990) 81], ovine, porcine, avian or even simian (example: SAV) origin. Preferably, the adenovirus of animal origin is a canine adenovirus, more particularly a CAV2 adenovirus [Manhattan strain or A26/61 (ATCC VR-800) for example]. Preferably, adenoviruses of human or canine or mixed origin are used within the framework of the invention.

The defective recombinant adenoviruses according to the invention can be prepared by any technique known to persons skilled in the art (Levrero et al., Gene 101 (1991) 195, EP 185 573; Graham, EMBO J. 3 (1984) 2917). In particular, they can be prepared by homologous recombination between an adenovirus and a plasmid carrying, inter alia, the glutathione peroxidase encoding DNA sequence. The homologous recombination occurs after co-transfection of the said adenoviruses and plasmid into an appropriate cell line. The cell line used should preferably (i) be transformable by the said elements and (ii) contain the sequences capable of complementing the defective adenovirus genome part, preferably in integrated form in order to avoid risks of recombination. As an example of a cell line, there may be mentioned the human embryonic kidney line 293 (Graham et al., J. Gen. Virol. 36 (1977) 59) which contains especially, integrated into its genome, the left-hand part of the genome of an Ad5 adenovirus (12%). Strategies for constructing vectors derived from adenoviruses have also been described in Applications Nos. FR 93 05954 and FR 93 08596 which are incorporated into the present application by reference.

Next, the adenoviruses which have multiplied are recovered and purified according to conventional molecular biology techniques as illustrated in the examples.

The particularly advantageous properties of the vectors of the invention stem especially from the construct used (defective adenovirus, deleted of certain viral regions), the promoter used for the expression of the glutathione peroxidase encoding sequence (viral or tissue-specific promoters preferably), and methods for administering the said vector, allowing efficient expression of the said enzyme in the appropriate tissues.

The present invention also relates to any use of an adenovirus as described above for the preparation of a pharmaceutical composition intended for the treatment and/or prevention of the abovementioned pathologies. More particularly it relates to any use of these adenoviruses for the preparation of a pharmaceutical composition intended for the treatment and/or prevention of neurodegenerative diseases such as for example Parkinson's disease, Alzheimer's disease, amyotrophic lateral sclerosis (ALS) and trisomy 21. They can also be advantageously used in the treatment of atherosclerosis, cardiovascular diseases, cirrhosis of the liver, diabetes, formation of cataracts, cerebral ischaemia, cranial traumas, respiratory distress syndrome (ARDS), diseases linked to an immune deficiency, cancers as well as in the aging process.

The present invention also relates to a pharmaceutical composition comprising one or more defective recombinant adenoviruses as described above. These pharmaceutical compositions may be formulated for topical, oral, parenteral, intranasal, intravenous, intramuscular, subcutaneous, intraocular or transdermal administration and the like. Preferably, the pharmaceutical compositions of the invention contain a pharmaceutically acceptable vehicle for an injectable formulation, especially for a direct injection into the patient. These may be in particular isotonic sterile solutions, or dry, especially freeze-dried, compositions which, upon addition, depending on the case, of sterilized water or physiological saline, allow the preparation of injectable solutions.

In this respect, the invention also relates to a method for treating neurodegenerative diseases comprising the administration, to a patient, of a recombinant adenovirus as defined above. More particularly, the invention relates to a method for treating neurodegenerative diseases comprising the stereotaxic administration of a recombinant adenovirus as defined above.

The doses of defective recombinant adenovirus used for the injection can be adjusted according to various parameters, and specially according to the mode of administration used, the relevant pathology or even the desired duration of treatment. Generally, the recombinant adenoviruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectivity of a virus solution, and is determined by infecting an appropriate cell culture and measuring, generally after 48 hours, the number of plaques of infected cells. The techniques for determining the pfu titre of a viral solution are well documented in the literature.

Another subject of the invention relates to any mammalian cell infected by one or more defective recombinant adenoviruses as described above. More particularly the invention relates to any human cell population infected by these adenoviruses. This may be in particular fibroblasts, myoblasts, hepatocytes, keratinocytes, endothelial cells, glial cells and the like.

The cells according to the invention can be obtained from primary cultures. These can be collected by any technique known to persons skilled in the art and then cultured under conditions permitting their proliferation. As regards more particularly fibroblasts, these can be easily obtained from biopsies, for example according to the technique described by Ham [Methods Cell. Biol. 21a (1980) 255]. These cells can be used directly for infection by adenoviruses, or preserved, for example by freezing, for establishing autologous libraries, for subsequent use. The cells according to the invention can also be secondary cultures which are obtained for example from pre-established libraries.

The cultured cells are then infected with the recombinant adenoviruses, so as to confer on them the capacity to produce glutathione peroxidase. The infection is carried out in vitro according to techniques known to persons skilled in the art. In particular, depending on the type of cells used and the desired copy number of virus per cell, persons skilled in the art can adjust the multiplicity of infection. It is clearly understood that these steps should be carried out under appropriate sterile conditions when the cells are intended for administration in vivo. The recombinant adenovirus doses used for the infection of the cells can be adjusted by persons skilled in the art according to the desired aim. The conditions described above for administration in vivo can be applied to infection in vitro.

Another subject of the invention relates to an implant comprising mammalian cells infected with one or more defective recombinant adenoviruses as described above, and an extracellular matrix. Preferably, the implants according to the invention comprise $10^5$ to $10^{10}$ cells. More preferably, they comprise $10^6$ to $10^8$ cells.

More particularly, in the implants of the invention, the extracellular matrix comprises a gelling compound and optionally a support permitting anchorage of the cells.

For the preparation of the implants according to the invention, various types of gelling agents can be used. The gelling agents are used for the inclusion of the cells in a matrix having the constitution of a gel, and to enhance the anchorage of the cells on the support, where appropriate. Various cell adhesion agents can therefore be used as gelling agents, such as especially collagen, gelatin, glucosaminoglycans, fibronectin, lectins, agarose and the like.

As indicated above the compositions according to the invention advantageously comprise a support permitting anchorage of the cells. The term anchorage designates any form of biological and/or chemical and/or physical interaction resulting in the adhesion and/or binding of the cells onto the support. Moreover, the cells can either cover the support used, or penetrate inside this support, or both. The use of a solid, non-toxic and/or biocompatible support is preferred within the framework of the invention. In particular, it is possible to use polytetrafluoroethylene (PTFE) fibres or a support of biological origin.

The implants according to the invention can be implanted at different sites in the body. In particular, the implantation can be carried out in the peritoneal cavity, in the subcutaneous tissue (suprapubic region, iliac or inguinal fossae, and the like), in an organ, a muscle, a tumour, the central nervous system or alternatively under a mucous membrane. The implants according to the invention are particularly advantageous in the sense that they make it possible to control the release of the therapeutic product in the body: this release is first determined by the multiplicity of infection and by the number of implanted cells. Next, the release can be controlled either by the removal of the implant, which permanently stops the treatment, or by the use of regulable expression systems, which make it possible to induce or to repress the expression of the therapeutic genes.

The present invention thus provides viral vectors which can be directly used in gene therapy, and which are particularly suitable and efficient for directing the expression of glutathione peroxidase in vivo. The present invention thus offers a new approach which is particularly advantageous for the treatment and/or prevention of many pathologies such as those mentioned above.

The adenoviral vectors according to the invention have, in addition, major advantages, linked especially to their very high efficiency of infection of the target cells, which make it possible to achieve infections with small volumes of viral suspension. Furthermore, infection with the adenoviruses of the invention is highly localized at the site of injection, which avoids the risks of diffusion to the neighbouring cerebral structures. This treatment may apply both to man and to any animal such as ovines, bovines, murines, domestic animals (dogs, cats and the like), horses, fish and the like.

It is perfectly possible, in addition, to envisage a simultaneous administration of an adenovirus according to the invention with at least a second adenovirus containing a gene encoding one of the forms of superoxide dismutase or catalase.

The examples and the single figure are presented below as a guide and do not limit the scope of the invention.

FIGURE

FIG. 1: representation of the enzymatic activity of the glutathione peroxidase obtained from cells 293 infected with 0 to 500 pfu/recombinant adenovirus cell encoding GPx (AdGPx) or β-galactosidase (Adβgal).

GENERAL MOLECULAR BIOLOGY TECHNIQUES

The methods conventionally used in molecular biology, such as preparative extractions of plasmid DNA, centrifugation of plasmid DNA in caesium chloride gradient, agarose or acrylamide gel electrophoresis, purification of DNA fragments by electroelution, phenol or phenol-chloroform extraction of proteins, ethanol or isopropanol precipitation of DNA in saline medium, transformation in *Escherichia coli* and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The pBR322- and pUC-type plasmids and the phages of the M13 series are of commercial origin (Bethesda Research Laboratories).

For the ligations, the DNA fragments can be is separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier.

The filling of the protruding 5' ends can be performed with the Klenow fragment of *E. coli* DNA polymerase I (Biolabs) according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method developed by Taylor et al. [Nucleic Acids Res. 13 (1985) 8749–8764] using the kit distributed by Amersham.

The enzymatic amplification of DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] can be performed using a DNA thermal cycler (Perkin Elmer Cetus) according to the specifications of the manufacturer.

The verification of the nucleotide sequences can be performed by the method developed by Sanger et al. [Proc. Natl. Acad. Sci. USA, 74 (1977) 5463–5467] using the kit distributed by Amersham.

EXAMPLES

Example 1

Procedure for the Construction of the Vector pLTRIX-bGPx

This vector contains the sequence encoding bovine GPx under the control of the RSV virus LTR, as well as sequences from the adenovirus which allow recombination in vivo. The cDNA used is described in [Mullenbach et al., Oxy-Radicals in Molecular Biology and Pathology, 313–326, (1988)].

The DNA is inserted into the BamHI site of a plasmid Bluescript. A polyadenylzation sequence was introduced into the XhoI site of this plasmid. The latter is identified by SK-bGPx-PolyA.

The vector pLTRIX-bGPx is obtained by introducing an insert obtained by cleavage of SK-bGPx-PolyA into the EcoRV site of the plasmid pLTRIX.

Example 2

Construction of Recombinant Adenoviruses Containing a Sequence Encoding Bovine Glutathione Peroxidase The vector pLTRIX-bGPx is linearized and cotransfected with a deficient adenoviral vector, into the helper cells (line 293) providing in trans the functions encoded by the adenovirus E1 regions (E1A and E1B).

More precisely, the Ad-bGPx adenovirus was obtained by homologous recombination in vivo between the mutant adenovirus Ad-dl1324 (Thimmappaya et al., Cell 31 (1982) 543) and the vector pLTR IX-bGPx, according to the following procedure: the plasmid pLTR IX-bGPx and the Ad-dl1324 adenovirus, linearized by the enzyme ClaI, were cotransfected into the line 293 in the presence of calcium phosphate, so as to allow the homologous recombination. The recombinant adenoviruses thus generated were selected by plaque purification. After isolation, the recombinant adenovirus DNA was amplified in the cell line 293, thereby giving a culture supernatant containing the unpurified recombinant defective adenovirus having a titre of about $10^{10}$ pfu/ml.

The viral particles are then purified by gradient centrifugation.

Example 3

Control of the Expression in vitro of GPx

For each test, an extract (0.5% triton) is produced from 300,000 cells 293 infected with 0 to 500 pfu/recombinant adenovirus cell encoding GPx or β-galactosidase. The enzymatic activity of glutathione peroxidase is evaluated according to the procedure of Flohé and Günzler (1984, Methods in Enzymology, Vol; 105, pp 114–121). The oxidized glutathione (GSSG) formed during the GPx reaction is constantly reduced by an excess of glutathione reductase activity for a constant level of reduced glutathione (GSH). The simultaneous oxidation of NADPH is monitored by spectrophotometry.

FIG. 1 presents the results obtained.

The invention claimed is:

1. A cultured human glial cell infected with a replication defective recombinant Ad5 human adenovirus, wherein said adenovirus comprises a cDNA sequence encoding a human glutathione peroxidase under the control of an RSV LTR promoter controlling expression in a glial cell, a sequence permitting encapsidation, and wherein an adenoviral E1 gene and at least one of the adenoviral L1–L5 genes are not functional.

2. The human glial cell according to claim 1, wherein the adenovirus further comprises ITRs, and wherein at least one of an adenoviral E2 or E4 genes is not functional.

3. A method of directing the expression of a human glutathione peroxidase in a glial cell according to claim 1, comprising infecting a glial cell with a replication defective recombinant Ad5 human adenovirus, wherein said adenovirus comprises a cDNA sequence encoding a human glutathione peroxidase under the control of an RSV LTR promoter controlling expression in a glial cell, a sequence permitting encapsidation, and a secretory signal, and wherein an adenoviral E1 gene and at least one of the adenoviral L1–L5 genes are not functional in said adenovirus.

4. The method according to claim 3, wherein the adenovirus further comprises ITRs, and wherein at least one of an adenoviral E2 or E4 genes is not functional.

* * * * *